(12) United States Patent
Lee et al.

(10) Patent No.: US 11,351,078 B2
(45) Date of Patent: Jun. 7, 2022

(54) METHOD FOR CLEANING AND STERILIZING EXCRETA HANDLING DEVICE AND EXCRETA HANDLING DEVICE USING SAME

(71) Applicant: CURACO, Inc., Seongnam-si (KR)

(72) Inventors: Hoon Sang Lee, Gwangju-si (KR); Ho Sang Lee, Seoul (KR)

(73) Assignee: CURACO, Inc., Seongnam-si (KR)

( * ) Notice: Subject to any disclaimer, the term of this patent is extended or adjusted under 35 U.S.C. 154(b) by 401 days.

(21) Appl. No.: 16/632,383

(22) PCT Filed: Jul. 25, 2018

(86) PCT No.: PCT/KR2018/008390
§ 371 (c)(1),
(2) Date: Jan. 20, 2020

(87) PCT Pub. No.: WO2019/022490
PCT Pub. Date: Jan. 31, 2019

(65) Prior Publication Data
US 2020/0230007 A1    Jul. 23, 2020

(30) Foreign Application Priority Data

Jul. 25, 2017 (KR) .......................... 10-2017-0093945

(51) Int. Cl.
*A61G 9/00* (2006.01)
*A61F 5/451* (2006.01)
(Continued)

(52) U.S. Cl.
CPC ................ *A61G 9/00* (2013.01); *A61F 5/451* (2013.01); *A61G 7/02* (2013.01); *A61G 2200/32* (2013.01); *A61G 2203/30* (2013.01); *E03D 9/00* (2013.01)

(58) Field of Classification Search
CPC . A61G 9/00; A61G 9/006; A61G 9/02; A61G 9/003
See application file for complete search history.

(56) References Cited

U.S. PATENT DOCUMENTS

2009/0260140 A1\* 10/2009 Birbara ................... A47K 11/12
4/144.1
2012/0066825 A1\* 3/2012 Birbara ................... A47K 11/12
4/309
(Continued)

FOREIGN PATENT DOCUMENTS

| JP | 2003-278219 A | 10/2003 |
|---|---|---|
| JP | 2010-148722 A | 7/2010 |

(Continued)

OTHER PUBLICATIONS

International Search Report of PCT/KR2018/008390 dated Nov. 27, 2018 from Korean Intellectual Property Office.

*Primary Examiner* — Christine J Skubinna
(74) *Attorney, Agent, or Firm* — Revolution IP, PLLC

(57) ABSTRACT

A method for cleaning and sterilizing an excreta handling device includes: positioning one end and the other end of the suction pipe on the same line; driving the pump to supply the cleaning water to a preset water level in the inner space through the first nozzle part; and maintaining, for a predetermined time, a state in which the cleaning water has been supplied to the preset water level, and then driving the suction part to suck the cleaning water contained in the inner space.

14 Claims, 13 Drawing Sheets

(51) Int. Cl.
*A61G 7/02* (2006.01)
*E03D 9/00* (2006.01)

(56) References Cited

U.S. PATENT DOCUMENTS

| | | | | |
|---|---|---|---|---|
| 2012/0110725 A1* | 5/2012 | Lee | ............................ | A61G 9/00 4/321 |
| 2013/0036544 A1* | 2/2013 | Lee | ......................... | A61G 9/003 4/443 |

FOREIGN PATENT DOCUMENTS

| KR | 10-2009-0039120 A | 4/2009 |
|---|---|---|
| KR | 10-2009-0039121 A | 4/2009 |
| KR | 10-2013-0011580 A | 1/2013 |
| KR | 10-1575140 B1 | 12/2015 |

* cited by examiner (a)

(b)

METHOD FOR CLEANING AND STERILIZING EXCRETA HANDLING DEVICE AND EXCRETA HANDLING DEVICE USING SAME

TECHNICAL FIELD

The present invention relates to a method for cleaning and sterilizing an excreta handling device and an excreta handling device using the same and, more specifically, to a method for cleaning and sterilizing an excreta handling device that can be easily and periodically cleaned by a user and an excreta handling device using the same.

BACKGROUND ART

An excreta handling device is a device that receives and handles excreta excreted from a user in the state where an excreta receiving part is seated in the user's body. Recently, as the number of the elderly or patients lying in sickbeds increases due to an increase in average life expectancy, the excreta handling device is appealing to people.

Such an excreta handling device should be periodically cleaned to be hygienically maintained, because bacteria may be easily propagated by excreta spattering against a rear space when in use or excreta attached to a suction pipe while sucking the excreta.

However, in order to clean the excreta handling device, components (excreta receiving part, suction pipe, discharge pipe, etc.) constituting the excreta handling device should be separated and manually cleaned, thus causing inconvenience. Likewise, in order to clean or sterilize the excreta handling device, the separated components should be a place with water supply and drain facilities, thus causing inconvenience.

Therefore, there is a need for a method for cleaning and sterilizing an excreta handling device that may be easily cleaned and sterilized without separating and moving the excreta handling device and an excreta handling device using the same.

PRIOR ART DOCUMENT (Patent Document 1) Korean Patent No. 10-1575140

DISCLOSURE

Technical Problem

Accordingly, the present invention has been made keeping in mind the above problems occurring in the related art, and is intended to provide a method for cleaning and sterilizing an excreta handling device that may be easily cleaned and sterilized without separating and moving the excreta handling device and an excreta handling device using the same.

The objects of the present invention are not limited to the above-mentioned objects, and other objects which are not mentioned above will be clearly understood by those skilled in the art from the following description.

Technical Solution

In order to accomplish the above-described object, the present invention provides a method for cleaning and sterilizing an excreta handling device, including positioning one end and the other end of the suction pipe on the same line, driving the pump to supply the cleaning water to a preset water level in the inner space through the first nozzle part, and maintaining, for a predetermined time, a state in which the cleaning water has been supplied to the preset water level, and then driving the suction part to suck the cleaning water contained in the inner space, the device having a main body that defines an inner space to receive excreta, a suction pipe that communicates with the inner space, an excreta receiving part that has a first nozzle part formed in the inner space and a first cleaning-water supply pipe supplying cleaning water to the first nozzle part, and a control module that has a suction part connected to the suction pipe to provide a suction force, and a cleaning-water storing part connected to the first cleaning-water supply pipe, with a pump being formed therein to provide a pumping force.

According to an embodiment of the invention, the supplying of the cleaning water to the preset water level in the inner space may include driving the pump to supply a first amount of cleaning water to the inner space; and driving the pump to supply a second amount of cleaning water to the inner space, the supplying of the second amount of cleaning water to the inner space may be slower in speed of supplying the cleaning water than the supplying of the first amount of cleaning water to the inner space.

According to an embodiment of the invention, the supplying of the first amount of cleaning water and the supplying of the second amount of cleaning water may be different from each other in output and driving time of the pump.

According to an embodiment of the invention, the excreta receiving part may further include a second nozzle part formed in the inner space, and a second cleaning-water supply pipe supplying the cleaning water to the second nozzle part, the second cleaning-water supply pipe being connected to the cleaning-water storing part, and the method may further include changing a direction of the second nozzle part such that a spray hole of the second nozzle part positioned in the inner space faces the inner space; driving the pump to supply the cleaning water to the second nozzle part; and driving the suction part to suck the cleaning water sprayed from the second nozzle part through the suction pipe.

According to an embodiment of the invention, the excreta receiving part may further include a third nozzle part formed in the inner space, and a third cleaning-water supply pipe supplying the cleaning water to the third nozzle part, the third cleaning-water supply pipe being connected to the cleaning-water storing part, and the method may further include driving the pump to supply the cleaning water to the third nozzle part; and driving the suction part to suck the cleaning water sprayed from the third nozzle part through the suction pipe.

According to an embodiment of the invention, the control module may further include a disinfectant supply part connected to the cleaning-water storing part, and the method may further include, prior to supplying the cleaning water to the preset water level in the inner space, driving the disinfectant supply part to put disinfectant into the cleaning-water storing part.

According to an embodiment of the invention, the supplying of the cleaning water to the preset water level in the inner space may include driving the pump to supply the cleaning water to the inner space; measuring the water level through a water level sensor formed in the inner space; and stopping driving the pump, if the measured water level is equal to or more than the preset water level.

According to an embodiment of the invention, the positioning of at least one end and the other end of the suction pipe on the same line may include tilting the excreta receiving part such that one end of the main body with which the suction pipe is coupled faces downwards; positioning one end and the other end of the suction pipe on the same line; and positioning an area excluding one end and the other end of the suction pipe under one end and the other end of the suction pipe.

In order to accomplish the above-described object, the present invention provides an excreta handling device including a main body defining an inner space to receive excreta, a suction pipe communicating with the inner space, an excreta receiving part having a first nozzle part formed in the inner space and a first cleaning-water supply pipe supplying cleaning water to the first nozzle part, a suction part connected to the suction pipe to provide a suction force, a pump formed to provide a pumping force, a cleaning-water storing part connected to the first cleaning-water supply pipe, a disinfectant supply part connected to the cleaning-water storing part to supply disinfectant to the cleaning-water storing part, a control panel having course selection means to select a preset cleaning course or sterilizing course, a control module having a controller that controls driving of the suction part, the pump, and the disinfectant supply part to perform a selected course as the cleaning course or the sterilizing course is selected through the control panel, a housing accommodating the control module therein, and a holder provided on an outer circumference of the housing, and tilting and seating the main body to position one end and the other end of the suction pipe on the same line, wherein the controller may perform driving the pump to supply a preset amount of cleaning water to the inner space through the first nozzle part, as the cleaning course is selected, and driving the suction part to suck the cleaning water contained in the inner space, after a preset time has passed.

According to an embodiment of the invention, the controller may perform driving the disinfectant supply part to put the disinfectant into the cleaning-water storing part, as the sterilizing course is selected, driving the pump to supply a preset amount of cleaning water to the inner space, and driving the suction part to suck the cleaning water contained in the inner space, after a preset time has passed.

In order to accomplish the above-described object, the present invention provides a method for cleaning and sterilizing an excreta handling device, including changing a direction of the nozzle part such that a spray hole of the nozzle part faces the inner space; driving the pump to supply the cleaning water to the nozzle part; and opening the valve to supply a preset amount of cleaning water to the inner space through the cleaning-water supply part, the device having a cleaning-water storing part connected to a faucet and storing cleaning water therein, a toilet bowl installed in front of the cleaning-water storing part and having an inner space and a siphon pipe that communicates with the inner space, a cleaning-water supply part provided in the toilet bowl, connected to the cleaning-water storing part via a first cleaning-water supply pipe, and supplying the cleaning water to the inner space, an excreta receiving part provided in the toilet bowl, connected to the cleaning-water storing part via a second cleaning-water supply pipe, and having a nozzle part that sprays cleaning water to a user, a pump providing a pumping force to supply water to the nozzle part, a valve provided between the cleaning-water storing part and the first cleaning-water supply pipe, and a control module connected to the cleaning-water storing part and having a disinfectant supply part that supplies excreta to the cleaning-water storing part.

According to an embodiment of the invention, the method may further include driving the disinfectant supply part to put the excreta into the cleaning-water storing part.

In order to accomplish the above-described object, the present invention provides an excreta handling device including a cleaning-water storing part connected to a faucet and storing cleaning water therein, a toilet bowl installed in front of the cleaning-water storing part and having an inner space and a siphon pipe that communicates with the inner space, a cleaning-water supply part provided in the toilet bowl, connected to the cleaning-water storing part via a first cleaning-water supply pipe, and supplying the cleaning water to the inner space, an excreta receiving part provided in the toilet bowl, connected to the cleaning-water storing part via a second cleaning-water supply pipe, and having a nozzle part that sprays cleaning water to a user, a pump providing a pumping force to supply water to the nozzle part, a valve provided between the cleaning-water storing part and the first cleaning-water supply pipe, a disinfectant supply part connected to the cleaning-water storing part, and supplying excreta to the cleaning-water storing part, a control panel having course selection means to select a preset cleaning course or sterilizing course, and a control module having a controller that controls driving of the cleaning-water supply part, the pump, and the disinfectant supply part to perform a selected course as the cleaning course or the sterilizing course is selected through the control panel, wherein the controller performs driving the pump to supply a preset amount of cleaning water to the nozzle part, as the cleaning course is selected, and driving the valve to supply the cleaning water to the inner space.

According to an embodiment of the invention, the controller may perform driving the disinfectant supply part to put the disinfectant into the cleaning-water storing part, as the sterilizing course is selected, driving the pump to supply a preset amount of cleaning water to the nozzle part, and driving the valve to supply the cleaning water to the inner space.

Advantageous Effects

According to an embodiment of the present invention, a path of an excreta handling device through which excreta and cleaning water pass can be nonstop cleaned and sterilized using a suction part, a pump and the like formed in the existing excreta handling device without separating the excreta handling device, thus improving a user's convenience.

Furthermore, according to an embodiment of the present invention, since cleaning water is sucked after a state where an excreta receiving part of an excreta handling device is filled with cleaning water is maintained for a predetermined time, dried excreta can be soaked in the cleaning water to be easily removed, thus improving cleaning and sterilizing efficiency.

It is to be understood that the effects of the present invention are not limited to the above-mentioned effects, and all effects deducible from the configuration of the invention described in the detailed description or the claims are included.

BEST MODE

Figure 1:
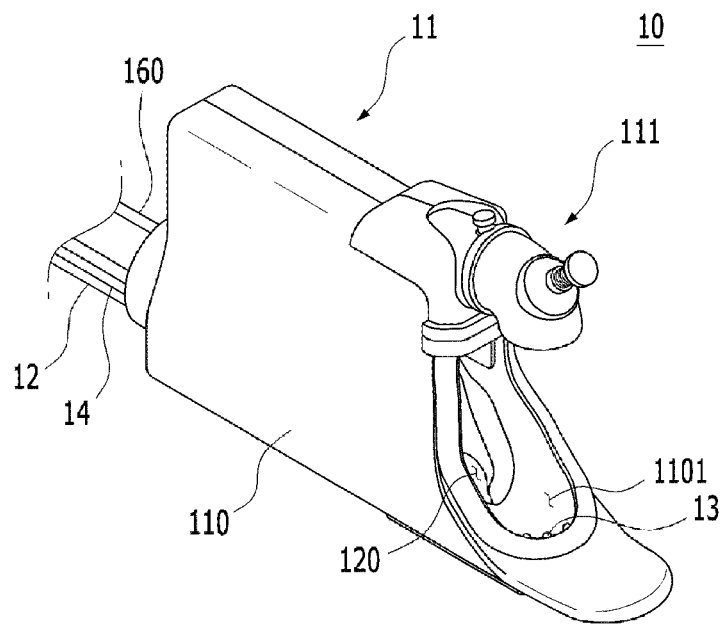
FIG. 1 is a diagram illustrating an excreta receiving part having a male module that is one of components of an excreta handling device according to a first embodiment of the present invention.
Figure 1:
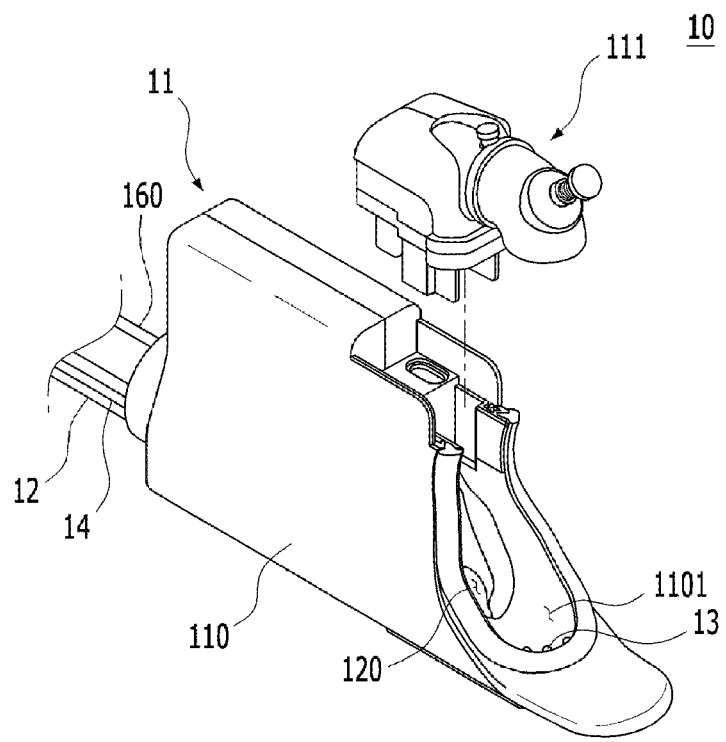

Hereinafter, the present invention will be described with reference to the accompanying drawings. This invention may, however, be embodied in many different forms and should not be construed as limited to the embodiments set forth herein. Further, it should be understood that parts which are not related to the present invention are omitted in the drawings for clarity of description. Like reference numerals designate like elements throughout the specification.

When the term "couple" or "connect" is used in the following description, it is intended to mean not only "directly coupled or connected to" but also "indirectly coupled or connected to" such as connected through another intervening element. In addition, the expression "a part includes a component" means that the part may further include another component without excluding another component, unless otherwise stated.

Terms used herein are merely for the purpose of describing specific embodiments, and are not intended to limit the invention. A singular form includes a plural from unless otherwise stated. Herein, terms such as "include" or "have" represent that one or more features, numbers, steps, operations, elements, components or combinations described in the specification exist, but do not exclude the possibility of the presence or addition of one or more of other features, numbers, steps, operations, elements, components or combinations thereof.

Hereinafter, embodiments of the present invention will be described in detail.

FIG. 1 is a diagram illustrating an excreta receiving part 10 having a male module 111 that is one of components of an excreta handling device 1 according to a first embodiment of the present invention.

Figure 2:
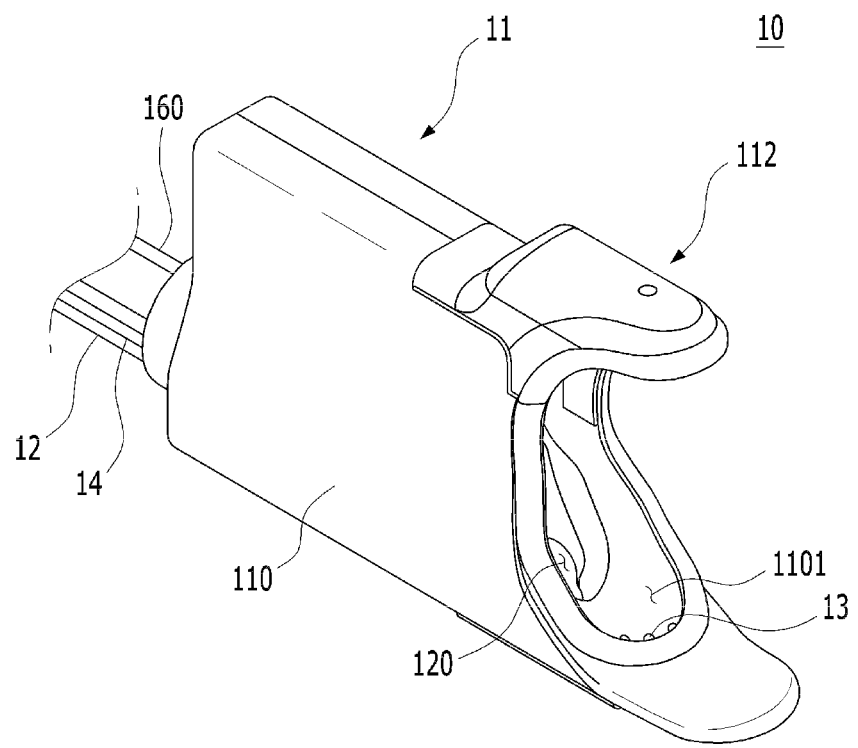
FIG. 2 is a diagram illustrating an excreta receiving part having a female module that is one of components of the excreta handling device according to the first embodiment of the present invention.
Figure 3:
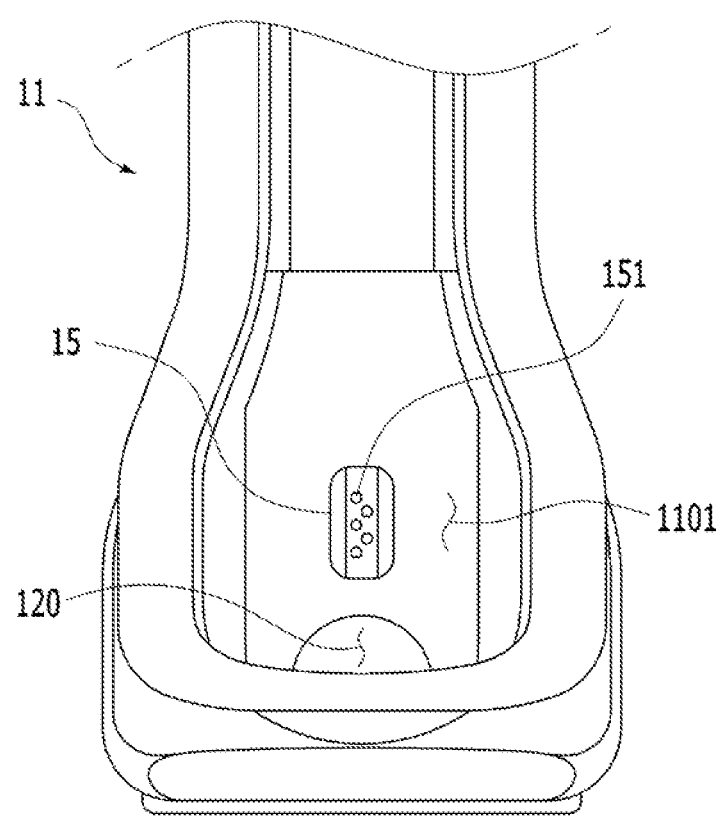
FIG. 3 is a diagram illustrating a body of FIG. 2.
Figure 4:
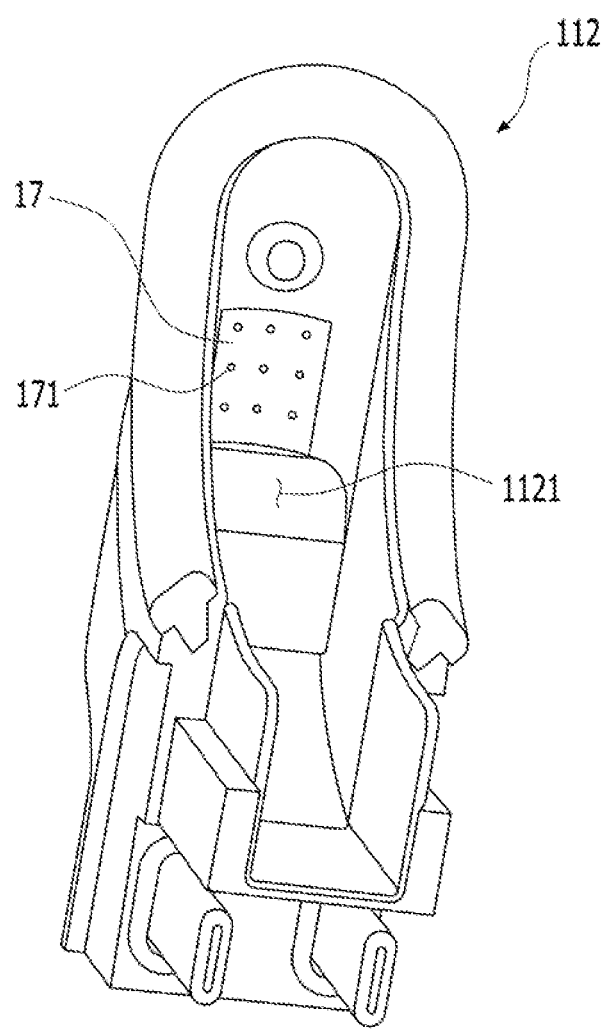
FIG. 4 is a diagram illustrating the female module of FIG. 2.

The excreta handling device 1 includes an excreta receiving part 10 and a control module 20 (see FIG. 4). In FIGS. 1 to 3, the excreta receiving part 10 will be described.

The excreta receiving part 10 according to an embodiment of the present invention includes a main body 11, a suction pipe 12, a first nozzle part 13, and a first cleaning-water supply pipe 14.

A user's buttocks are seated on the main body 11. The main body is opened towards the genital organ and buttocks of a human body, thus defining an inner space that receives excreta that is excreted from a user's body.

When in use, after the main body 11 is placed between the legs and comes into close contact with the buttocks, a user's legs may extend to both sides of the main body 11. FIG. 1 is a diagram of the excreta receiving part 10 when seen from above. The excreta receiving part is an area with which the user's buttocks come into close contact.

To be more specific, the main body 11 includes a body 110, and a male module 111 or a female module 112 coupled with the body 110.

FIG. 1A illustrates a configuration in which the body 110 and the male module 111 are coupled with each other, and FIG. 1B illustrates a configuration in which the body 110 and the male module 111 are separated from each other.

Hereinafter, for the convenience of description, a direction in which the male module 111 is provided is defined as an upper side, while an opposite direction is defined as a lower side.

A user's body is seated on the body 110, which is opened towards the buttocks of the human body, thus defining a first inner space 1101 that receives the excreta excreted from the user's body. Here, the suction pipe 12 having a suction path 120 to suck the excreta may be coupled to a first inner space 1101. The suction pipe 12 communicates with the first inner space 1101, and is connected to a suction part 21 that will be described later.

The first nozzle part 13 is a component that supplies cleaning water to the first inner space 1101 to drain the excreta received in the first inner space 1101 to the suction pipe 12, and is formed in a lower portion of the first inner space 1101. The first nozzle part 1102 may be connected via the first cleaning-water supply pipe 14 to a cleaning-water storing part 22 (see FIG. 5) that will be described later, thus receiving cleaning water from the cleaning-water storing part 22.

The excreta receiving part 10 may further include a second nozzle part 15 (see FIG. 3) and a second cleaning-water supply pipe (see FIG. 5) that supplies cleaning water to the second nozzle part 15. The second nozzle part 15 may be formed in an area of the body 110, and may spray cleaning water to clean the buttocks of the human body. The second cleaning-water supply pipe 16 may be connected to the cleaning-water storing part 22.

The male module 111 is opened towards the genital organ of the human body, thus defining a second inner space (not shown) that receives urine excreted from a user's body. Here, the second inner space may communicate with the first inner space 1101 to allow urine contained in the second inner space to move to the first inner space 1101. The above-described inner space of the main body 11 includes the first inner space 1101 and the second inner space.

Furthermore, the excreta receiving part 10 may further include a third nozzle part 17 (see FIG. 4), and a third cleaning-water supply pipe 18 (see FIG. 5) that supplies cleaning water to the third nozzle part 17. The third nozzle part 17 may be formed in an area of the male module 111 or the female module 112 that will be described later, thus spraying cleaning water to clean the genital organ of the human body. The third cleaning-water supply pipe 18 may be connected to the cleaning-water storing part 22. Although FIG. 4 shows only a configuration where the third nozzle part 17 is formed in an area of the female module 112, it is natural that the third nozzle part 17 be formed in the male module 111.

FIG. 2 is a diagram illustrating the excreta receiving part 10 having the female module 112 that is one of components of the excreta handling device 1 according to the first embodiment of the present invention.

If a user of the excreta receiving part 10 is a female, the female module 112 may be coupled to the body 110 and then used. That is, the excreta receiving part 10 of the present invention may be changed depending on a user's gender.

FIG. 3 is a diagram illustrating the body 110 of FIG. 2, and shows the second nozzle part 15. The second nozzle part 15 may spray the cleaning water transmitted through the second cleaning-water supply pipe 16 onto the buttocks to clean the buttocks of the human body, and may be positioned in the first inner space 1101 of the body 110.

One or more spray holes 151 may be formed in an outer circumference of the second nozzle part 15. Here, the second nozzle part 15 may be formed in the shape of a cylinder, and the spray holes 151 may be formed in a side of the cylinder.

Furthermore, the second nozzle part 15 may be coupled to the body 110 to be rotatable around a central axis, so that the second nozzle part may be rotated in response to a control signal of a controller 25 that will be described later. That is, a direction in which cleaning water is supplied (or sprayed) may be changed by the rotation of the second nozzle part 15. The second nozzle part 15 may be connected to the cleaning-water storing part 22 via the second cleaning-water supply pipe 16, so that cleaning water may be transmitted from the cleaning-water storing part 22 to the second nozzle part.

Although not shown in FIG. 3, a water level sensor 113 (see FIG. 5) may be provided in the inner space of the excreta receiving part 10 to measure the water level of the cleaning water. The water level sensor 113 is connected to the controller 25 to transmit the measured water level to the controller 25.

FIG. 4 is a diagram illustrating the female module 112 of FIG. 2. The female module 112 may have a second inner space 1121 that may communicate with the first inner space 1101.

The female module 112 may have a third nozzle part 17 that supplies the cleaning water transmitted from the cleaning-water storing part 22 so as to clean the genital organ of the human body. One or more spray holes 171 may be formed in the third nozzle part 17, which may be formed on an upper surface of the second inner space 1121. The third nozzle part 17 may be connected to the cleaning-water storing part 22, which will be described later, via the third cleaning-water supply pipe 18 to receive the cleaning water from the cleaning-water storing part that will be described later.

Figure 5:
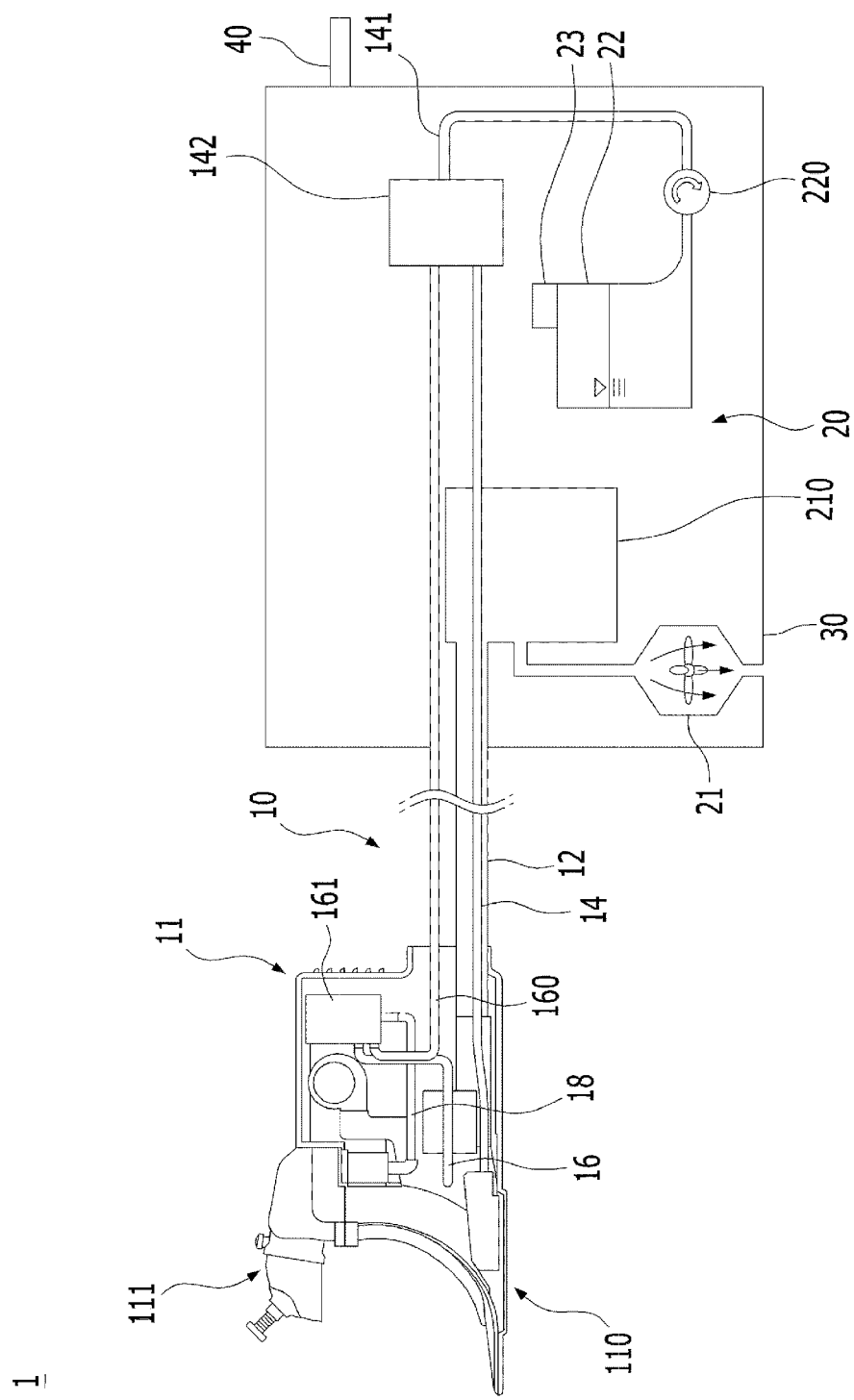
FIG. 5 is a diagram illustrating the excreta handling device according to the first embodiment of the present invention.
Figure 6:
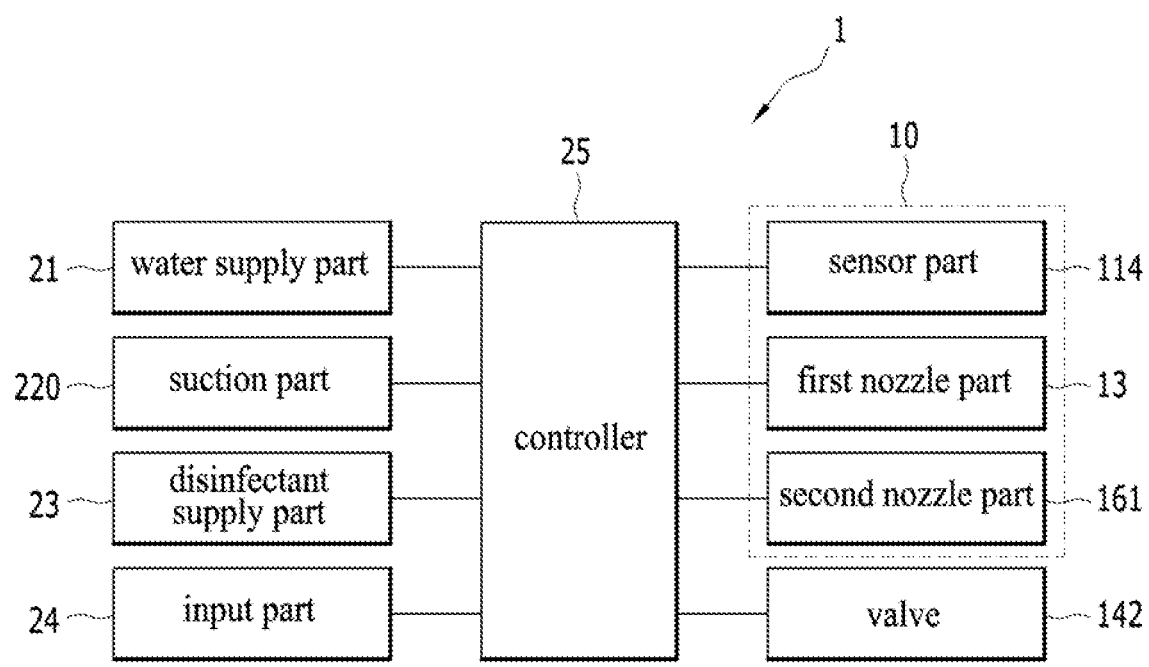
FIG. 6 is a diagram illustrating the configuration of the excreta handling device according to the first embodiment of the present invention.

FIG. 5 is a diagram illustrating the excreta handling device 1 according to the first embodiment of the present invention, and FIG. is a diagram illustrating the configuration of the excreta handling device 1 according to the first embodiment of the present invention.

As described above, the excreta handling device 1 includes the excreta receiving part 10 and a control module 20.

Since the excreta receiving part 10 has been described with reference to FIGS. 1 to 4, a detailed description thereof will be omitted herein.

The control module 20 is a component that controls the cleaning and sterilization of the excreta receiving part 10, and is connected to the excreta receiving part 10. The control module 20 may include a suction part 21 and a cleaning-water storing part 22. The control module may further include a disinfectant supply part 23, a control panel 24, and a controller 25.

The suction part 21 is a component that provides a suction force to the suction pipe 12, and is connected to the suction pipe 12 to suck excreta or cleaning water contained in an inner space of the suction pipe 12 or the main body 11 (hereinafter, referred to as the inner space). An excreta storing member 210 may be formed on suction part 21.

The excreta storing member 210 is a component that stores excreta sucked through the suction pipe 12, and has a storing space. The suction part 21 discharges the air of the excreta storing member 210 to the outside to reduce the pressure of the storing space, thus moving matter contained in the suction pipe 12 or the inner space towards the storing space.

The cleaning-water storing part 22 is a component that stores cleaning water and supplies the stored cleaning water to the inner space. A pump 220 may be formed in the cleaning-water storing part to provide a pumping force. The cleaning-water storing part 22 may be connected to the first cleaning-water supply pipe 14, and may be controlled by the controller 25.

According to an embodiment of the present invention, a first connection pipe 141 may be formed between the pump 220 and the first cleaning-water supply pipe 14, and a first valve 142 may be formed on a junction of the first connection pipe 141 and the first cleaning-water supply pipe 14 to control the opening and closing of the first cleaning-water supply pipe 14. The first valve 142 may be controlled by the controller 25.

The above-described second cleaning-water supply pipe 16 and third cleaning-water supply pipe 18 may be connected to the first valve 142 with a second connection pipe 160 therebetween. That is, the second cleaning-water supply pipe 16 and the third cleaning-water supply pipe 18 may branch from the second connection pipe 160.

Furthermore, a second valve 161 may be formed on a junction between each of the second cleaning-water supply pipe 16 and the third cleaning-water supply pipe 18 and the second connection pipe 160 to control the opening and closing of the second cleaning-water supply pipe 16 and the third cleaning-water supply pipe 18.

Here, the second valve 161 may be formed in the main body 11, and may be controlled by the controller 25.

The disinfectant supply part 23 is a component that supplies disinfectant to the cleaning-water storing part 22, and may be coupled to the cleaning-water storing part 22. When the disinfectant is supplied to the cleaning-water storing part 22, the cleaning water stored in the cleaning-water storing part 22 may be changed into disinfecting solution.

The control panel 24 is a component that receives a user's command signal to select a cleaning course or a sterilizing course, and then transmits the signal to the controller 25.

The controller 25 is a component that controls the suction part 21, the cleaning-water storing part 22, the first valve 142, the second valve 161, and the disinfectant supply part 23. Furthermore, if a user selects the cleaning course or the sterilizing course via the control panel 24, the controller 25 controls the suction part 21, the cleaning-water storing part 22, the first valve 142, the second valve 161, and the disinfectant supply part 23 to perform a preset cleaning course or sterilizing course.

If the cleaning course is selected via the control panel 24, the controller 25 drives the pump 220 of the cleaning-water storing part 22 and controls the first valve 142 to open the first cleaning-water supply pipe 14, thus supplying the cleaning water to a preset water level in the inner space through the first nozzle part 13. After a preset time has passed, the suction part 21 is driven to suck the cleaning water contained in the inner space and the suction pipe 12.

Since the suction part 21 is driven after a preset time has passed, a state in which cleaning water is filled is maintained for a predetermined time, so that the excreta remaining in the suction pipe 12 may be soaked and thereby cleaning efficiency may be improved. Furthermore, according to the present invention, it is possible to clean the excreta handling device 1 using the pump 220, the suction part 21, and the controller 25 provided in the existing excreta handling device 1 without a cleaning device, so that it is unnecessary to provide a separate cleaning device.

The supply of the cleaning water to a preset water level by the controller 25 may be the supply of a preset amount of cleaning water or the control of the cleaning-water supply by measuring the water level through the water level sensor 113.

In the case of supplying the preset amount of cleaning water, the controller 25 may control the pump 220 of the cleaning-water storing part 22 and the first valve 142, thus supplying a first amount of cleaning water through the first cleaning-water supply pipe 14 into the inner space at a first speed, and supplying a second amount of cleaning water into the inner space at a second speed that is slower than the first speed. Here, when the first amount of cleaning water and the second amount of cleaning water are supplied to the inner space, the cleaning water may be filled to a preset water level in the inner space.

In other words, the cleaning water that is to be filled to the preset water level is supplied in two stages: the cleaning water is supplied quickly at an initial stage, and thereafter is supplied slowly. Although it is described herein that the cleaning water is supplied in two stages, the cleaning water may be supplied in three or more stages. The number of stages for supplying the cleaning water may be freely changed.

Meanwhile, the second speed is slower than the speed at which the cleaning water passes from the suction pipe 12 to the excreta storing member 210. Thus, even if the cleaning water is continuously supplied after being filled to the preset water level, the cleaning water exceeding the preset water level passes to the excreta storing member 210 connected to the suction pipe 12 due to the height of the suction pipe. Thus, no cleaning water is discharged out of the excreta handling device 1 beyond the preset water level. Here, the controller 25 may control the supply speed and supply amount of the cleaning water, by the preset output and driving time of the pump 220.

In the case of measuring the water level through the water level sensor 113 and then supplying the cleaning water, the controller 25 may control the pump 220 of the cleaning-water storing part 22 and the first valve 142, according to the water level value measured from the water level sensor 113. To be more specific, the controller 25 may control the pump 220 and the first valve 142 to supply the cleaning water through the first cleaning-water supply pipe 14 to the inner space. If the controller receives the water level value measured from the water level sensor 113 and the measured water level value is equal to or more than the preset water level, the controller controls to stop driving the pump 220 and cause the first valve 142 to close the first cleaning-water supply pipe 14.

After a preset time has passed, the suction part 21 is driven to suck the cleaning water contained in the inner space and the suction pipe 12. Thereafter, the controller 25 drives the second nozzle part 15 so that the spray hole 151 of the second nozzle part 15 faces the inner space, and drives the pump 220, the first valve 142, and the second valve 161 so that the cleaning water is supplied to the second cleaning-water supply pipe 16, thus supplying a preset amount of cleaning water to the second nozzle part 15, and drives the suction part 21 to suck the cleaning water contained in the inner space and the suction pipe 12. Here, the pump 220 and the suction part 21 may be simultaneously driven.

Subsequently, the controller 25 drives the pump 220 of the cleaning-water storing part 22, the first valve 142, and the second valve 161 to supply the cleaning water to the third cleaning-water supply pipe 18, thus supplying a preset amount of cleaning water to the third nozzle part 17, and drives the suction part 21 to suck the cleaning water contained in the inner space and the suction pipe 12. Here, the pump 220 and the suction part 21 may be simultaneously driven.

As such, while the cleaning water is supplied through the first cleaning-water supply pipe 14 to the inner space, the first cleaning-water supply pipe 14 and the first nozzle part 13 may be cleaned by the flow of the cleaning water. While the cleaning water fed into the inner space fills the suction pipe 12 and an area of the inner space and is sucked by the suction part 21, the suction pipe 12 and the inner space may be cleaned by the flow of the cleaning water.

Furthermore, while the cleaning water is supplied through the second cleaning-water supply pipe 16 and the third cleaning-water supply pipe 18 to the second nozzle part 15 and the third nozzle part 17, the second nozzle part 15, the third nozzle part 17, the second cleaning-water supply pipe 16, and the third cleaning-water supply pipe 18 may be cleaned by the flow of the cleaning water. In this case, the spray hole 151 of the second nozzle part 15 is arranged to face a wall surface defining the inner space, thus allowing the wall surface to be cleaned. Furthermore, while the cleaning water fed from the second nozzle part 15 and the third nozzle part 17 is sucked by the suction part 21, the suction pipe 12 may be cleaned. That is, the present invention may nonstop clean all paths through which the excreta and the cleaning water pass.

Meanwhile, the operation of the controller 25 may be repeated one or more times.

If the sterilizing course is selected through the control panel 24, the controller 25 drives the disinfectant supply par 23 that will be described later, thus putting the disinfectant into the cleaning-water storing part 22, and drives the pump 220 of the cleaning-water storing part 22, and controls the first valve 142 to open the first cleaning-water supply pipe 14, thus supplying a preset amount of cleaning water to the inner space, and drives the suction part 21 after a preset time has passed, thus sucking the cleaning water contained in the inner space and the suction pipe 12. Here, since the cleaning water is mixed with the disinfectant, the mixture may serve as a disinfecting solution. Since the sterilizing course is equal to the cleaning course except for the driving of the disinfectant supply part 23, a detailed description thereof will be omitted.

As such, the disinfectant may be supplied to the cleaning-water storing part 22, so that the cleaning-water storing part may be sterilized. While the cleaning water is supplied through the first cleaning-water supply pipe 14 to the inner space, the first cleaning-water supply pipe 14 and the first nozzle part 13 may be sterilized by the flow of the cleaning water. While the cleaning water supplied to the inner space fills the suction pipe 12 and an area of the inner space and is sucked through the suction part 21, the suction pipe 12 and the inner space may be sterilized by the flow of the cleaning water.

Furthermore, while the cleaning water is supplied through the second cleaning-water supply pipe 16 and the third cleaning-water supply pipe 18 to the second nozzle part 15 and the third nozzle part 17, the second nozzle part 15, the third nozzle part 17, the second cleaning-water supply pipe 16, and the third cleaning-water supply pipe 18 may be sterilized by the flow of the cleaning water. Here, the spray hole 151 of the second nozzle part 15 faces the wall surface defining the inner space, thus allowing the wall surface to be sterilized. Furthermore, while the cleaning water fed from the second nozzle part 15 and the third nozzle part 17 is sucked by the suction part 21, the suction pipe 12 may be sterilized. That is, the present invention may nonstop sterilize all paths through which the excreta and the cleaning water pass.

According to an embodiment of the present invention, a housing 30 may be formed to store all or some of the suction part 21 of the control module 20, the cleaning-water storing part 22, the disinfectant supply part 23, the first connection pipe 141, the second connection pipe 160, the suction pipe 12, and the first cleaning-water supply pipe 14.

Furthermore, one end and the other end of the suction pipe 12 (hereinafter referred to as ends of the suction pipe) may be positioned on the same line on the outer circumference of the housing 30, and a holder 40 on which the main body 11 is tilted and seated may be formed such that an area of the suction pipe 12 excluding one end and the other end of the suction pipe 12 (hereinafter referred to as an area of the suction pipe) is positioned under the ends of the suction pipe 12. That is, when the main body 11 is seated on the holder 40, it is unnecessary to separately adjust the tilting of the main body 11 and the height of the suction pipe.

The main body 11 is tilted, the ends of the suction pipe 12 are positioned on the same line, and an area of the suction pipe 12 is positioned under the ends of the suction pipe 12, so that the cleaning water supplied to the inner space may flow into the suction pipe 12, and the cleaning water may be transmitted to one end of the suction pipe 12 connected to the suction part 21. That is, according to the present invention, the suction pipe 12 may be filled with the cleaning water by adjusting the height of the suction pipe 12 even if one end of the suction pipe 12 is not closed. Since the suction pipe 12 is filled with the cleaning water, the excreta hardened on the suction pipe 12 may be soaked.

Figure 7:
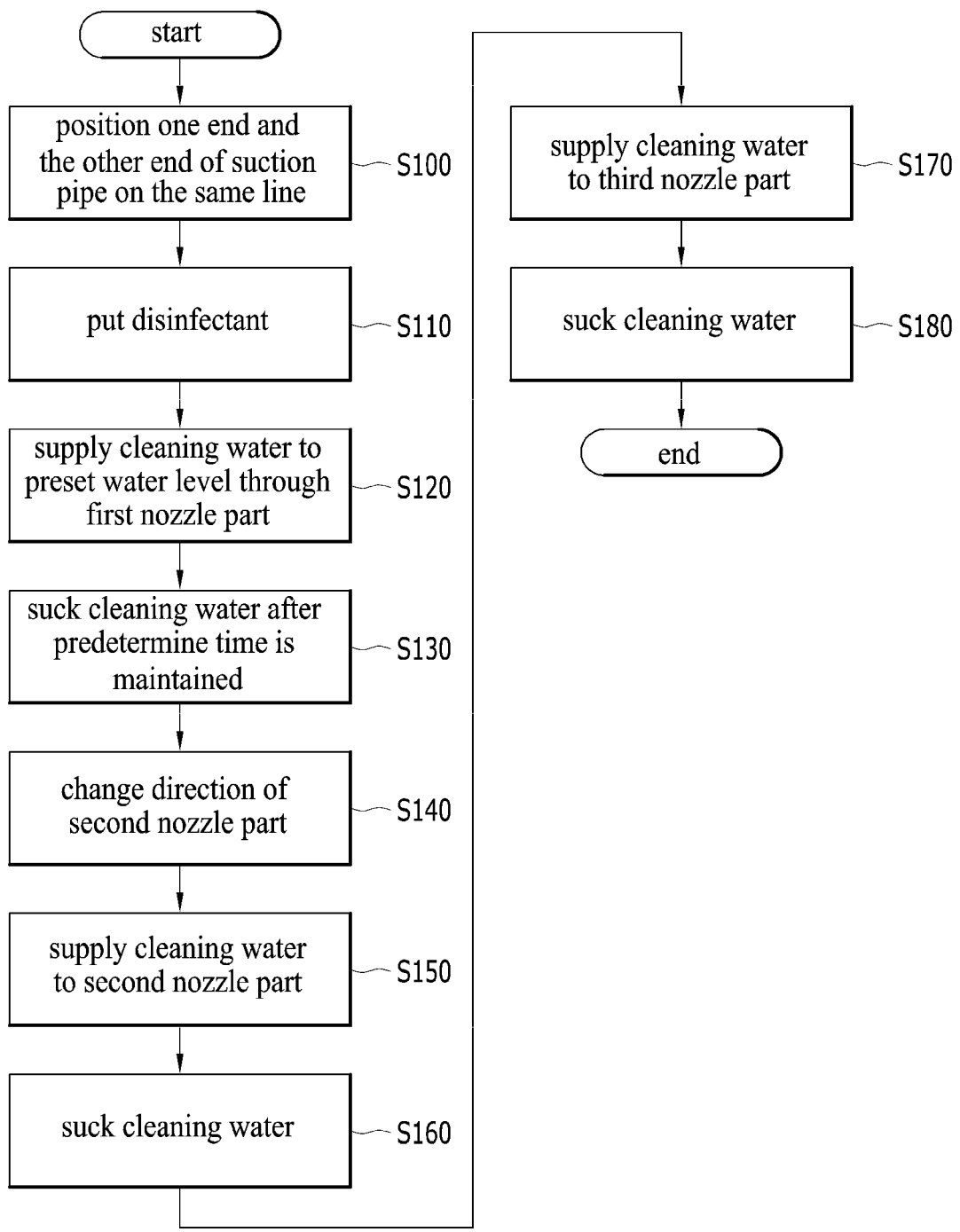
FIG. 7 is a flowchart illustrating a method for cleaning and sterilizing an excreta handling device according to the first embodiment of the present invention.

Hereinafter, a method for cleaning and sterilizing the excreta handling device 1 will be described with reference to FIGS. 1 to 6. FIG. 7 is a flowchart illustrating the method for cleaning and sterilizing the excreta handling device 1 according to the first embodiment of the present invention.

The method for cleaning and sterilizing the excreta handling device 1 according to the first embodiment of the present invention may include a step S100 of positioning one end and the other end of the suction pipe 12 on the same line, a step S120 of driving the pump 220 to supply the cleaning water through the first nozzle part 13 to a preset water level in the inner space of the main body 11, and a step S130 of driving the suction part 21 to suck the cleaning water contained in the inner space and the suction pipe 12, after a state where the cleaning water is supplied to the preset water level in the inner space is maintained for a predetermined time.

According to an embodiment of the present invention, after the step S100 of positioning one end and the other end of the suction pipe 12 on the same line, a step S110 of driving the disinfectant supply part 23 to put the disinfectant into the cleaning-water storing part 22 may be further included. In this regard, steps S110 to S130 may be performed by the controller 25.

The controller 25 may drive the disinfectant supply part 23 to change the cleaning water so that it serves as the disinfecting solution at step S110, supply a preset amount of the changed cleaning water to the inner space of the main body 11 or supply the cleaning water to a preset water level by measuring the water level through a water level sensor and controlling the supply of the cleaning water at step S120, and drive the suction part 21 to suck the cleaning water contained in the inner space and the suction pipe 12 after a predetermined time has passed at step S130.

Here, if a driving signal is applied from the controller 25, the disinfectant supply part 23 may be set to supply a certain amount of disinfectant to the cleaning-water storing part 22, or to supply a certain amount of disinfectant to the cleaning-water storing part 22 at a predetermined period. According to an embodiment of the present invention, the disinfectant supply part may be operated simultaneously with the pump 220.

Figure 8:
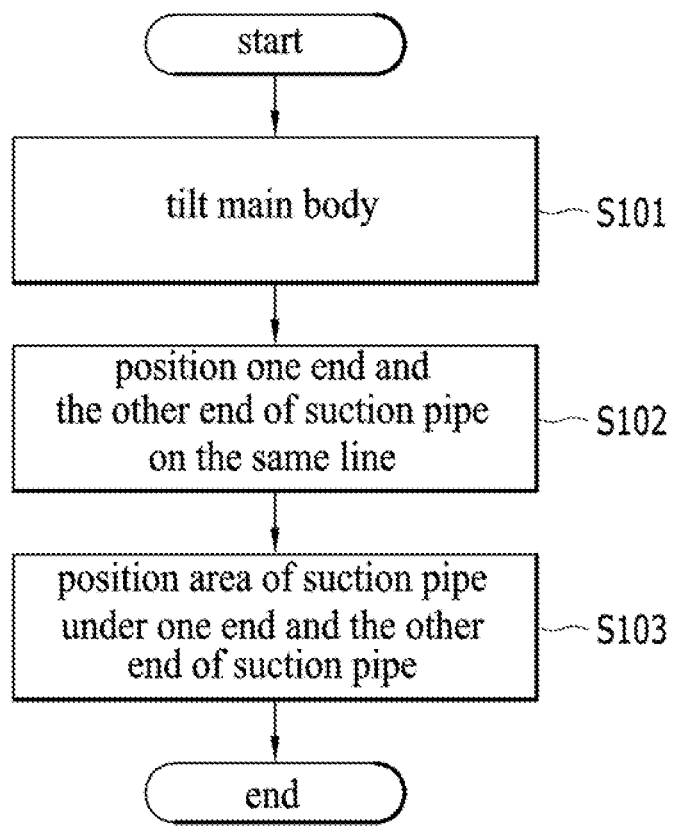
FIG. 8 is a detailed flowchart illustrating an embodiment of step S100 of FIG. 7.

Referring to FIG. 8, the step S100 of positioning one end and the other end of the suction pipe 12 on the same line includes a step S101 of tilting the main body 11 so that one end of the main body 11 to which the suction pipe 12 is coupled faces downwards, a step S102 of positioning one end and the other end of the suction pipe 12 on the same line, and a step S103 of positioning an area excluding one end and the other end of the suction pipe 12 under one end and the other end of the suction pipe 12.

Thus, the cleaning water contained in the inner space may flow into the suction pipe 12, and the cleaning water may be transmitted and filled to one end of the suction pipe 12 to which the suction part 21 is connected. According to an embodiment of the present invention, the step S100 of positioning one end and the other end of the suction pipe 12 on the same line may be a step of fixing the main body 11 to the above-described holder 40.

Figure 9:
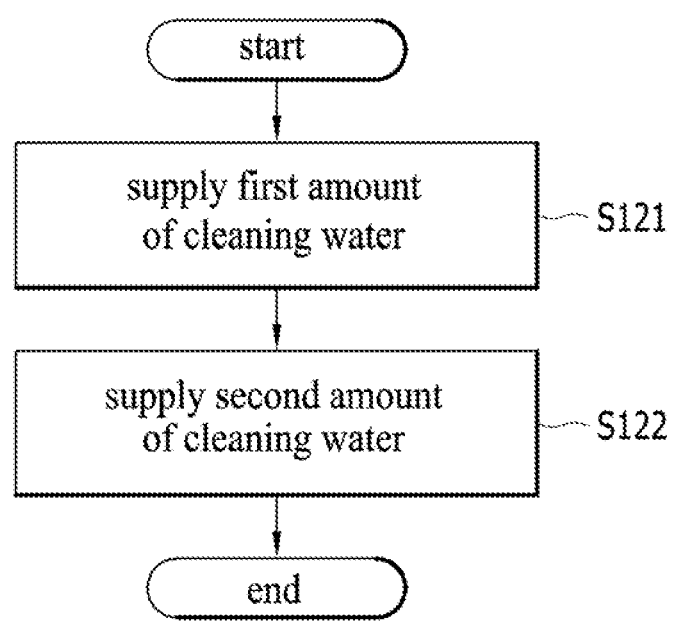
FIG. 9 is a detailed flowchart illustrating an embodiment of step S120 of FIG. 7.

Referring to FIG. 9, the step S120 of supplying the cleaning water to the preset water level in the inner space may include a step S121 of supplying a first amount of cleaning water to the inner space by driving the pump 220 of the cleaning-water storing part 22, and a step S122 of supplying a second amount of cleaning water to the inner space by driving the pump 220 again, after the first amount of cleaning water has been supplied.

Here, the step S121 of supplying the second amount of cleaning water to the inner space may be slower in speed of supplying the cleaning water than the step S122 of supplying the first amount of cleaning water to the inner space. That is, in the initial stage, the cleaning water is supplied quickly. After the cleaning water is filled to some extent, the cleaning water is supplied slowly. Thus, it is possible to prevent the cleaning water in the inner space from overflowing or spattering out of the main body 11 in the process of supplying the cleaning water.

The steps S121 and S122 may be performed by the controller 25. The controller 25 may supply the preset first amount of cleaning water to the inner space by driving the pump 220 at step S121, and may supply the preset second amount of cleaning water to the inner space at step S122.

Figure 10:
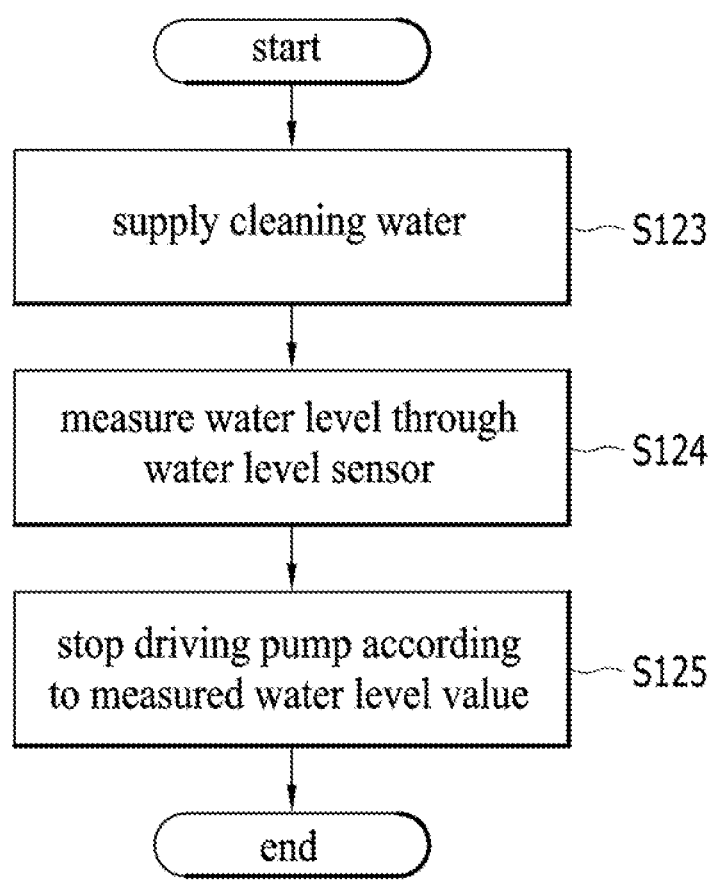
FIG. 10 is a detailed flowchart illustrating another embodiment of step S120 of FIG. 7.

Referring to FIG. 10, according to another embodiment of the present invention, the step S120 of supplying the cleaning water through the first nozzle part 13 to the preset water level in the inner space may include a step S123 of supplying the cleaning water to the inner space, a step S124 of measuring the water level through the water level sensor 113 installed in the inner space, and a step S125 of stopping driving the pump 220 if a water level measuring value is equal to or more than a preset water level. Thus, the excreta handling device 1 of the present invention may precisely supply the cleaning water to a preset water level.

The steps S123 to S125 may be performed by the controller 25. The controller 25 supplies the cleaning water to the inner space by driving the pump 220 of the cleaning-water storing part 22 at step S123, and receives the measured water level value of the inner space from the water level sensor 113 at step S124. After the water level value is received, the controller 25 determines whether the measured water level value is equal to or more than a preset water level at step S125. If the measured water level value is equal to or more than the preset water level, the driving of the pump 220 is stopped. On the other hand, if the measured water level value is less than the preset water level, the driving of the pump 220 is maintained.

Furthermore, according to an embodiment of the present invention, the method for cleaning and sterilizing the excreta handling device 1 may include a step S140 of changing a direction of the second nozzle part 15 such that the spray hole 151 of the second nozzle part 15 faces the inner wall of the inner space, after the step S130 of sucking the cleaning water contained in the inner space, a step S150 of supplying the cleaning water to the second nozzle part 15, and a step S160 of sucking the cleaning water contained in the inner space through the suction pipe 12. The inner wall defining the inner space may be cleaned or sterilized through steps S140 to S160.

The steps S140 to S160 may be performed by the controller 25. The controller 25 changes the direction of the nozzle such that the spray hole 151 of the second nozzle part 15 faces the inner wall by controlling the second nozzle part 15 at step S140, and supplies the cleaning water to the second nozzle part 15 by driving the pump 220 for a predetermined time at step S150, and sucks the cleaning water discharged from the second nozzle part 15 by driving the suction part 21 at step S160.

According to the embodiment of the present invention, the method for cleaning and sterilizing the excreta handling device 1 may further include, after the step S120 of sucking the cleaning water contained in the inner space or the step S160 of sucking the cleaning water contained in the inner space through the suction pipe 12, a step S170 of supplying the cleaning water to the third nozzle part 17 and a step S180 of sucking the cleaning water contained in the inner space through the suction pipe 12. Through the steps S170 and S180, the third nozzle part 17 may be cleaned or sterilized.

The steps S170 and S180 may be performed by the controller 25. The controller 25 may supply the cleaning water to the third nozzle part 17 by driving the pump 220 for a predetermined time at step S170, and may suck the cleaning water discharged from the third nozzle part 17 by driving the suction part 21 at step S180.

According to the embodiment of the invention, the excreta handling device can be cleaned and sterilized using the suction part 21, the pump 220 and the like formed in the existing excreta handling device 1 without separating the excreta handling device 1, thus improving a user's convenience.

Furthermore, according to the embodiment of the present invention, since the cleaning water is sucked after a state where the suction pipe 12 and the main body 11 of the excreta handling device 1 are filled with the cleaning water is maintained for the predetermined time, the dried excreta can be soaked in the cleaning water to be easily removed, thus improving the cleaning and sterilizing efficiency.

Figure 11:
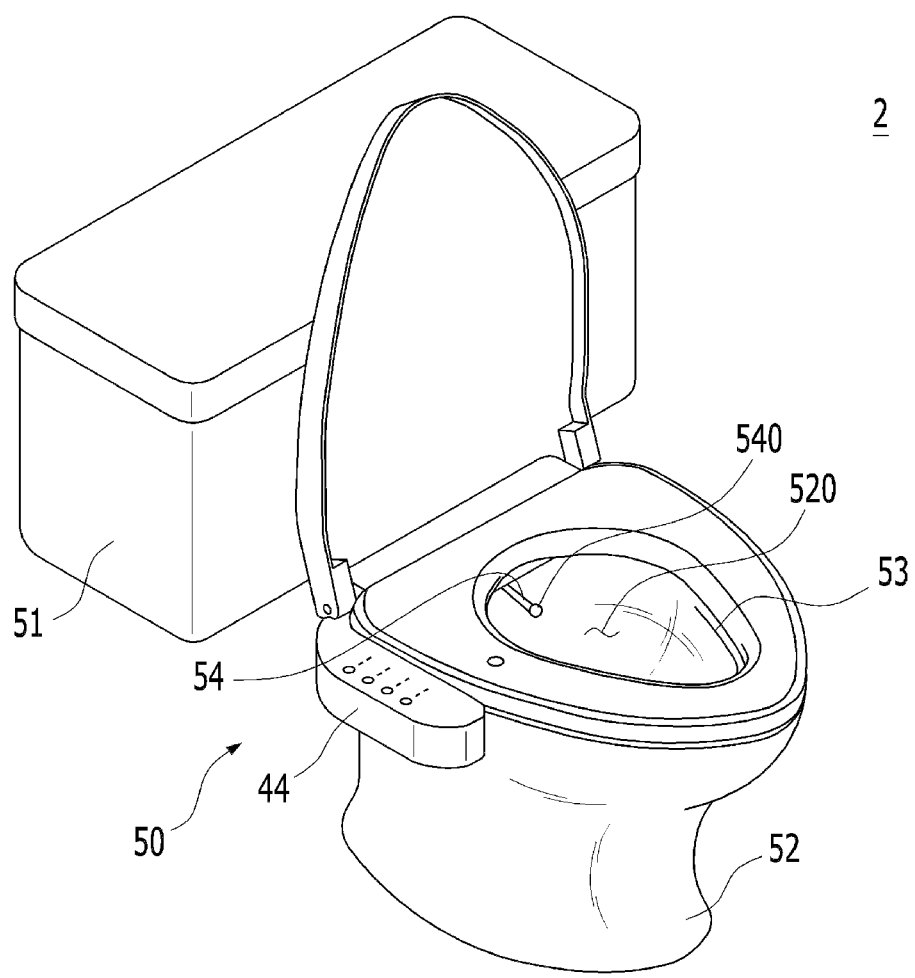
FIG. 11 is a diagram illustrating an excreta handling device according to a second embodiment of the present invention.

FIG. 11 is a diagram illustrating an excreta handling device 2 according to a second embodiment of the present invention, and FIG. is a diagram illustrating the configuration of the excreta handling device 2 according to the second embodiment of the present invention.

The excreta handling device 2 according to the second embodiment of the present invention includes an excreta receiving part 50 and a control module 60.

The excreta receiving part 50 is a common toilet seat, and includes a cleaning-water storing part 51 that is connected to a faucet via a water pipe and stores cleaning water therein, and a toilet bowl 52 that includes an inner space 520 to receive excreta and a siphon pipe (not shown) communicating with the inner space.

Here, when a certain amount of cleaning water is supplied to the inner space 520 of the toilet bowl 52, the cleaning water contained in the inner space 520 is discharged to the outside connected to a siphon along the siphon pipe (not shown), and the excreta is also discharged to the outside along with the cleaning water. That is, unlike the excreta receiving part 10 of the first embodiment, since the excreta and the cleaning water of the inner space 520 are moved by siphon pipe effects, a separate suction part is not required.

The excreta receiving part 50 includes a cleaning-water supply part 53, a first cleaning-water supply pipe (not shown), a nozzle part 54, and a second cleaning-water supply pipe (not shown).

The cleaning-water supply part 53 is a component that supplies water to the inner space 520, and is formed in the inner space 520. The first cleaning-water supply pipe is a component that is connected to the cleaning-water storing part 51 and the cleaning-water supply part 53 to transmit the cleaning water of the cleaning-water storing part 51 to the cleaning-water supply part 53. Here, a valve 61 of a control module 60 that will be described later is provided between the cleaning-water storing part 51 and the first cleaning-water supply pipe, thus controlling the supply of the cleaning water to the first cleaning-water supply pipe.

The nozzle part 54 is a component that sprays the cleaning water onto a user, and is formed in the inner space 520. A second cleaning-water supply pipe is a component that is connected to the cleaning-water storing part 51 and the nozzle part 54 to transmit the cleaning water of the cleaning-water storing part 51 to the nozzle part 54. Here, a pump 62 of the control module 60 that will be described later is provided between the cleaning-water storing part 51 and the second cleaning-water supply pipe, thus controlling the supply of the cleaning water to the second cleaning-water supply pipe, and simultaneously adjusting the spray force of the cleaning water sprayed to the nozzle part 54.

The control module 60 is a component that controls the cleaning and sterilization of the excreta receiving part 50, and is connected to the excreta receiving part 50. The control module 60 may include the valve 61 and the pump 62, and may further include a disinfectant supply part 63, a control panel 64, and a controller 65.

The valve 61 is provided between the cleaning-water storing part 51 and the first cleaning-water supply pipe to control the opening and closing of the first cleaning-water supply pipe. Here, the valve 61 may be controlled by the controller 65.

The pump 62 is provided between the cleaning-water storing part 51 and the second cleaning-water supply pipe, and provides a pumping force so that the cleaning water stored in the cleaning-water storing part 51 moves to the second cleaning-water supply pipe.

The disinfectant supply part 63 is a component that supplies the disinfectant to the cleaning-water storing part 51, and may be coupled to the cleaning-water storing part 51. In the case of supplying the disinfectant to the cleaning-water storing part 51, the cleaning water stored in the cleaning-water storing part 51 may be changed into the disinfecting solution.

The control panel 64 is a component that receives a user's command signal selecting the cleaning course or the sterilizing course and then transmits the signal to the controller 65.

The controller 65 is a component that controls the valve 61, the pump 62, the disinfectant supply part 63, and the nozzle part 54. Furthermore, if the user selects the cleaning course or the sterilizing course through the control panel 64, the controller 65 controls the valve 61, the pump 62, the disinfectant supply part 63, and the nozzle part 54 to perform a preset cleaning course or sterilizing course.

If the selection of the cleaning course is inputted from a user through the control panel 64, the controller 65 drives the nozzle part 54 so that the spray hole 540 of the nozzle part 54 faces the inner space 520, and drives the pump 62 to supply a preset amount of cleaning water from the cleaning-water storing part 51 through the second cleaning-water supply pipe to the nozzle part 54, and drives the valve 61 to supply a preset amount of cleaning water to the cleaning-water supply part 53. Here, the valve 61 and the pump 62 may be simultaneously driven.

Meanwhile, the preset amount of cleaning water supplied to the cleaning-water supply part 53 may be a sufficient amount of cleaning water to occur a siphon phenomenon in the excreta receiving part.

Since the cleaning water is contained in the cleaning-water storing part 51, the cleaning-water storing part 51 may be cleaned. While the cleaning water is supplied through the second cleaning-water supply pipe to the nozzle part 54, the second cleaning-water supply pipe and the nozzle part 54 may be cleaned by the flow of the cleaning water. In addition, while the cleaning water is supplied through the first cleaning-water supply pipe to the cleaning-water supply part 53, the first cleaning-water supply pipe and the cleaning-water supply part 53 may be cleaned by the flow of the cleaning water.

Furthermore, while the cleaning water provided to the nozzle part 54 and the cleaning-water supply part 53 is supplied to the inner space 520, the inner space 520 may be cleaned. Since the cleaning water flows along the siphon pipe, the siphon pipe may also be cleaned. That is, the present invention may nonstop clean all paths through which the excreta and the cleaning water pass.

Meanwhile, since the spray hole 540 of the nozzle part 54 is changed to face the inner space 520, the cleaning water is not sprayed to the outside of the excreta receiving part 50.

If the selection of the sterilizing course is inputted from a user through the control panel 64, the controller 65 drives the disinfectant supply part 63 to put the disinfectant into the cleaning-water storing part 51, drives the nozzle part 54 so that the spray hole 540 of the nozzle part 54 faces the inner space 520, drives the pump 62 to supply a preset amount of cleaning water from the cleaning-water storing part 51 through the second cleaning-water supply pipe to the nozzle part 54, and drives the valve 61 to supply a preset amount of cleaning water to the cleaning-water supply part 53. Since the sterilizing course is the same as the cleaning course except for the driving of the disinfectant supply part 63, a detailed description thereof will be omitted. Here, since the cleaning water is mixed with the disinfectant, the mixture may serve as the disinfecting solution.

Since the disinfectant is supplied to the cleaning-water storing part 51 as such, the cleaning-water storing part 51 may be sterilized. While the cleaning water is supplied through the second cleaning-water supply pipe to the nozzle part 54, the second cleaning-water supply pipe and the nozzle part 54 may be sterilized by the flow of the cleaning water. Further, while the cleaning water is supplied through the first cleaning-water supply pipe to the cleaning-water supply part 53, the first cleaning-water supply pipe and the cleaning-water supply part 53 may be sterilized by the flow of the cleaning water.

Furthermore, while the cleaning water provided to the nozzle part 54 and the cleaning-water supply part 53 is supplied to the inner space 520, the inner space 520 may be sterilized. Since the cleaning water flows along the siphon pipe, the siphon pipe may also be sterilized. That is, the present invention may nonstop clean all paths through which the excreta and the cleaning water pass.

Figure 12:
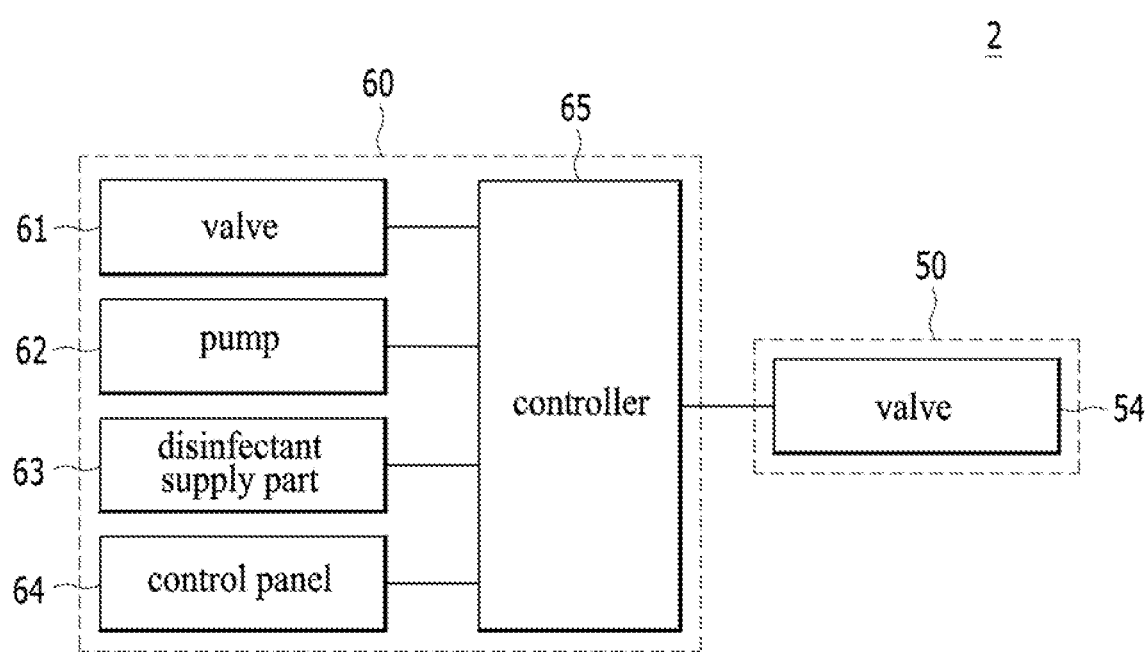
FIG. 12 is a diagram illustrating the configuration of the excreta handling device according to the second embodiment of the present invention.
Figure 13:
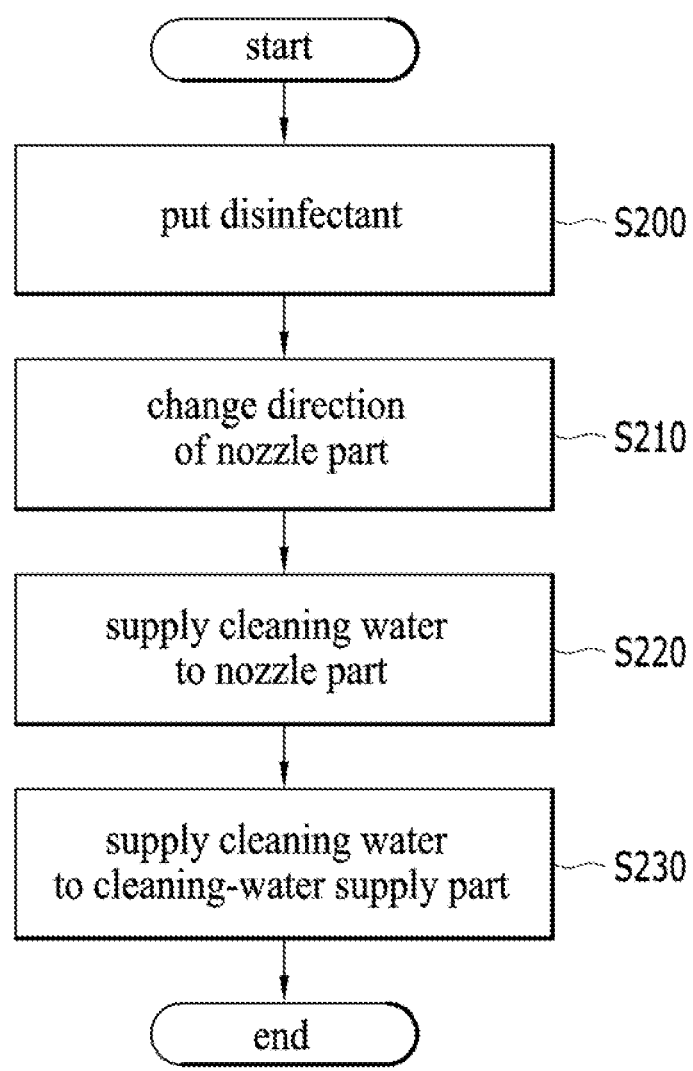
FIG. 13 is a flowchart illustrating a method for cleaning and sterilizing an excreta handling device according to the second embodiment of the present invention.

Hereinafter, a method for cleaning and sterilizing the excreta handling device 2 will be described with reference to FIGS. 11 and 12. FIG. 13 is a flowchart illustrating the method for cleaning and sterilizing the excreta handling device 2 according to the second embodiment of the present invention.

The method for cleaning and sterilizing the excreta handling device 2 according to the second embodiment of the present invention includes a step S210 of changing a direction of the nozzle part 54 such that the spray hole 540 of the nozzle part 54 faces the inner space 520, a step S220 of supplying the cleaning water to the nozzle part 54, and a step S220 of supplying the cleaning water to the cleaning-water supply part 53.

According to an embodiment of the present invention, a step S200 of putting the disinfectant into the cleaning-water storing part 51 by driving the disinfectant supply part 63 may be further included, prior to the step S110 of changing the nozzle part 54. The steps S200 to S230 may be performed by the controller 65.

The controller 65 changes the cleaning water to act as the disinfecting solution by driving the disinfectant supply part 63 at step S200, changes the direction of the nozzle so that the spray hole 540 of the nozzle part 54 faces the inner space 520 by controlling the nozzle part 54 at step S210, and then supplies the cleaning water to the nozzle part 54 by driving the pump 62 for a preset time at step S220, and supplies the cleaning water to the cleaning-water supply part 53 by driving to open the valve 61 for a predetermined time at step S230. At this time, the controller 65 may control the valve 61 to supply a sufficient amount of cleaning water to occur the siphon phenomenon in the excreta receiving part 50 at step S230.

According to the embodiment of the invention, the excreta handling device 2 can be cleaned and sterilized using the valve 61, the pump 62 and the like formed in the existing excreta handling device 2 without separating the excreta handling device 2, thus improving a user's convenience.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. Therefore, the above-described embodiments of the present invention are not restrictive but are illustrative. For example, each component described as a single form may be implemented in a divided form, while components described as the divided form may be implemented in a combined form.

It is to be understood that the scope of the invention is determined by the appended claims, and all changes falling within bounds of the claims or equivalence of the bounds are included in the scope of the invention.

The invention claimed is:

1. A method for cleaning and sterilizing an excreta handling device having a main body that defines an inner space to receive excreta, a suction pipe that communicates with the inner space, an excreta receiving part that has a first nozzle part formed in the inner space and a first cleaning-water supply pipe supplying cleaning water to the first nozzle part, and a control module that has a suction part connected to the suction pipe to provide a suction force, and a cleaning-water storing part connected to the first cleaning-water supply pipe, with a pump being formed therein to provide a pumping force, the method comprising:
    positioning one end and the other end of the suction pipe on the same line;
    driving the pump to supply the cleaning water to a preset water level in the inner space through the first nozzle part; and
    maintaining, for a predetermined time, a state in which the cleaning water has been supplied to the preset water level, and then driving the suction part to suck the cleaning water contained in the inner space.

2. The method of claim 1, wherein the supplying of the cleaning water to the preset water level in the inner space comprises:
    driving the pump to supply a first amount of cleaning water to the inner space; and
    driving the pump to supply a second amount of cleaning water to the inner space,
    the supplying of the second amount of cleaning water to the inner space is slower in speed of supplying the cleaning water than the supplying of the first amount of cleaning water to the inner space.

3. The method of claim 2, wherein the supplying of the first amount of cleaning water and the supplying of the second amount of cleaning water are different from each other in output and driving time of the pump.

4. The method of claim 1, wherein the excreta receiving part further comprises a second nozzle part formed in the inner space, and a second cleaning-water supply pipe supplying the cleaning water to the second nozzle part, the second cleaning-water supply pipe being connected to the cleaning-water storing part, and the method further comprises:
    changing a direction of the second nozzle part such that a spray hole of the second nozzle part positioned in the inner space faces the inner space;
    driving the pump to supply the cleaning water to the second nozzle part; and
    driving the suction part to suck the cleaning water sprayed from the second nozzle part through the suction pipe.

5. The method of claim 1, wherein the excreta receiving part further comprises a third nozzle part formed in the inner space, and a third cleaning-water supply pipe supplying the cleaning water to the third nozzle part, the third cleaning-water supply pipe being connected to the cleaning-water storing part, and the method further comprises:
    driving the pump to supply the cleaning water to the third nozzle part; and
    driving the suction part to suck the cleaning water sprayed from the third nozzle part through the suction pipe.

6. The method of claim 1, wherein the control module further comprises a disinfectant supply part connected to the cleaning-water storing part, and the method further comprises:
    prior to supplying the cleaning water to the preset water level in the inner space, driving the disinfectant supply part to put disinfectant into the cleaning-water storing part.

7. The method of claim 1, wherein the supplying of the cleaning water to the preset water level in the inner space comprises:
    driving the pump to supply the cleaning water to the inner space;
    measuring the water level through a water level sensor formed in the inner space; and
    stopping driving the pump, if the measured water level is equal to or more than the preset water level.

8. The method of claim 1, wherein the positioning of at least one end and the other end of the suction pipe on the same line comprises:
    tilting the excreta receiving part such that one end of the main body with which the suction pipe is coupled faces downwards;
    positioning one end and the other end of the suction pipe on the same line; and
    positioning an area excluding one end and the other end of the suction pipe under one end and the other end of the suction pipe.

9. An excreta handling device comprising:
    a main body defining an inner space to receive excreta,
    a suction pipe communicating with the inner space,
    an excreta receiving part having a first nozzle part formed in the inner space and a first cleaning-water supply pipe supplying cleaning water to the first nozzle part,
    a suction part connected to the suction pipe to provide a suction force,
    a pump formed to provide a pumping force,
    a cleaning-water storing part connected to the first cleaning-water supply pipe,
    a disinfectant supply part connected to the cleaning-water storing part to supply disinfectant to the cleaning-water storing part,
    a control panel having course selection means to select a preset cleaning course or sterilizing course,
    a control module having a controller that controls driving of the suction part, the pump, and the disinfectant supply part to perform a selected course as the cleaning course or the sterilizing course is selected through the control panel,
    a housing accommodating the control module therein, and
    a holder provided on an outer circumference of the housing, and tilting and seating the main body to position one end and the other end of the suction pipe on the same line,
    wherein the controller performs driving the pump to supply a preset amount of cleaning water to the inner space through the first nozzle part, as the cleaning course is selected, and driving the suction part to suck the cleaning water contained in the inner space, after a preset time has passed.

10. The excreta handling device of claim 9, wherein the controller performs driving the disinfectant supply part to put the disinfectant into the cleaning-water storing part, as the sterilizing course is selected, driving the pump to supply a preset amount of cleaning water to the inner space, and driving the suction part to suck the cleaning water contained in the inner space, after a preset time has passed.

11. A method for cleaning and sterilizing an excreta handling device having a cleaning-water storing part connected to a faucet and storing cleaning water therein, a toilet bowl installed in front of the cleaning-water storing part and having an inner space and a siphon pipe that communicates with the inner space, a cleaning-water supply part provided in the toilet bowl, connected to the cleaning-water storing part via a first cleaning-water supply pipe, and supplying the cleaning water to the inner space, an excreta receiving part provided in the toilet bowl, connected to the cleaning-water storing part via a second cleaning-water supply pipe, and having a nozzle part that sprays cleaning water to a user, a pump providing a pumping force to supply water to the nozzle part, a valve provided between the cleaning-water storing part and the first cleaning-water supply pipe, and a control module connected to the cleaning-water storing part and having a disinfectant supply part that supplies excreta to the cleaning-water storing part, the method comprising:
changing a direction of the nozzle part such that a spray hole of the nozzle part faces the inner space;
driving the pump to supply the cleaning water to the nozzle part; and
opening the valve to supply a preset amount of cleaning water to the inner space through the cleaning-water supply part.

12. The method of claim 11, further comprising:
prior to changing the direction of the nozzle part, driving the disinfectant supply part to put the excreta into the cleaning-water storing part.

13. An excreta handling device comprising:
a cleaning-water storing part connected to a faucet and storing cleaning water therein,
a toilet bowl installed in front of the cleaning-water storing part and having an inner space and a siphon pipe that communicates with the inner space,
a cleaning-water supply part provided in the toilet bowl, connected to the cleaning-water storing part via a first cleaning-water supply pipe, and supplying the cleaning water to the inner space,
an excreta receiving part provided in the toilet bowl, connected to the cleaning-water storing part via a second cleaning-water supply pipe, and having a nozzle part that sprays cleaning water to a user,
a pump providing a pumping force to supply water to the nozzle part,
a valve provided between the cleaning-water storing part and the first cleaning-water supply pipe,
a disinfectant supply part connected to the cleaning-water storing part, and supplying excreta to the cleaning-water storing part,
a control panel having course selection means to select a preset cleaning course or sterilizing course, and
a control module having a controller that controls driving of the cleaning-water supply part, the pump, and the disinfectant supply part to perform a selected course as the cleaning course or the sterilizing course is selected through the control panel,
wherein the controller performs driving the pump to supply a preset amount of cleaning water to the nozzle part, as the cleaning course is selected, and driving the valve to supply the cleaning water to the inner space.

14. The excreta handling device of claim 13, wherein the controller performs driving the disinfectant supply part to put the disinfectant into the cleaning-water storing part, as the sterilizing course is selected, driving the pump to supply a preset amount of cleaning water to the nozzle part, and driving the valve to supply the cleaning water to the inner space.

* * * * *